United States Patent
Fischer et al.

(10) Patent No.: US 6,953,280 B2
(45) Date of Patent: Oct. 11, 2005

(54) CALORIMETER

(75) Inventors: Ulrich Fischer, Zurich (CH); Konrad Hungerbühler, Wintersingen (CH); Max Wohlwend, Samstagern (CH); Andreas Zogg, Zurich (CH)

(73) Assignee: Eidgenössische Technische Hochschule Zürich, Zürich (CH)

( * ) Notice: Subject to any disclaimer, the term of this patent is extended or adjusted under 35 U.S.C. 154(b) by 140 days.

(21) Appl. No.: 10/129,481

(22) PCT Filed: Aug. 23, 2001

(86) PCT No.: PCT/CH01/00516
§ 371 (c)(1),
(2), (4) Date: Sep. 16, 2002

(87) PCT Pub. No.: WO02/21089
PCT Pub. Date: Mar. 14, 2002

(65) Prior Publication Data
US 2003/0058918 A1 Mar. 27, 2003

(30) Foreign Application Priority Data
Sep. 4, 2000 (EP) .............................. 00810797

(51) Int. Cl.⁷ .............................................. G01K 17/00
(52) U.S. Cl. .............................. 374/33; 374/31; 374/34
(58) Field of Search .............................. 374/31, 33, 34; 422/51; 436/147

(56) References Cited

U.S. PATENT DOCUMENTS

| | | | | |
|---|---|---|---|---|
| 2,733,602 A | * | 2/1956 | Jackson, Jr. et al. | 374/33 |
| 2,982,132 A | * | 5/1961 | Mendlowitz | 374/33 |
| 3,718,437 A | * | 2/1973 | Paloniemi | 374/33 |
| 3,768,973 A | * | 10/1973 | Wasilewski | 374/33 |
| 4,130,016 A | * | 12/1978 | Walker | 374/34 |
| 4,178,800 A | * | 12/1979 | Thomann | 374/33 |
| 4,511,263 A | * | 4/1985 | Prosen | 374/33 |
| 4,614,721 A | | 9/1986 | Goldberg | |
| 4,859,077 A | * | 8/1989 | Ito et al. | 374/33 |
| 4,892,707 A | * | 1/1990 | Stockton et al. | 374/33 |
| 5,604,132 A | * | 2/1997 | Capuano et al. | 422/81 |
| 5,707,149 A | * | 1/1998 | Freire et al. | 374/33 |
| 5,876,118 A | * | 3/1999 | Vogel | 374/33 |
| 6,028,172 A | * | 2/2000 | Stepaniuk et al. | 422/99 |
| 6,572,263 B1 | * | 6/2003 | Refalo et al. | 374/31 |
| 6,608,678 B1 | * | 8/2003 | Potyrailo et al. | 356/301 |

FOREIGN PATENT DOCUMENTS

| | | | |
|---|---|---|---|
| DE | 30 49 105 A1 | 7/1982 | |
| EP | 275042 A2 | * 7/1988 | 374/31 |
| JP | 55144518 A | * 11/1980 | 374/31 |

OTHER PUBLICATIONS

Schildknecht, J., "Reaction calorimeter for application in chemical process industries: Performance and Calibration", *Thermochemica Acta*, vol. 49, 1981 (Amsterdam, Belgium), p. 101–110.

Schildknecht, J., "Development and Application of a 'Mini Pilot Reactor Calorimeter'", *Preprints* vol. III/139–143, 2$^{nd}$ International Symposium on Loss Prevention & Safety Promotion in the Process Industries, (Heidelberg, Germany), 1981.

* cited by examiner

*Primary Examiner*—G. Bradley Bennett
*Assistant Examiner*—Mirellys Jagan
(74) *Attorney, Agent, or Firm*—Browdy and Neimark, P.L.L.C.

(57) ABSTRACT

The invention relates to a calorimeter comprising a reactor (1) that is fitted in an intermediate thermostat (2). Said intermediate thermostat (2) cooperates with an external thermostat (3) and comprises a metal block (4) as the heat transfer medium. The inventive calorimeter can be produced at lower costs than those comprising a double-walled reaction vessel and allows especially IR probe analysis.

6 Claims, 1 Drawing Sheet

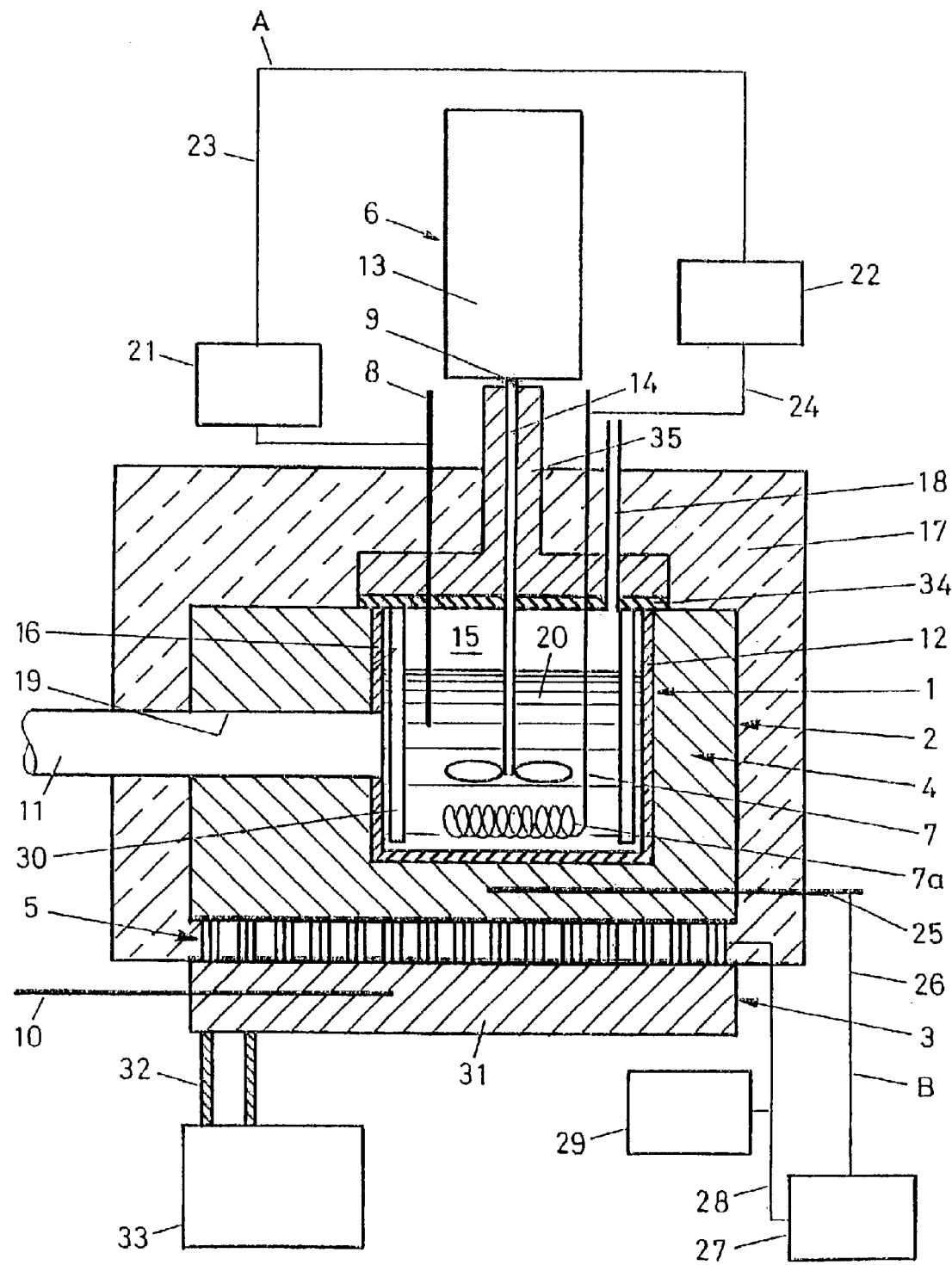

CALORIMETER

The present invention relates to a calorimeter having a reactor according to the preamble of claim 1.

BACKGROUND OF THE INVENTION

1. Field of Invention

Calorimeters have been known for a long time and are used to screen reactions, particularly during the process development in the chemical industry. In doing so, chemical reactions are examined regarding their thermodynamics and kinetics. Essential parameters are the reaction enthalpy, the thermal capacity, and the specific reaction rates, for example.

Calorimeters measure heat flows of chemical reactions and physical conversions. Isothermal, adiabatic, isoperibolic and temperature-programmed variants are being offered. When examining chemical reactions to determine thermokinetic data, isothermal measuring conditions are often preferred in practical operation. Isothermal reaction conditions are particularly advantageous when calometry and online analytics are combined, as the corresponding signals can change as a function of the temperature. Ensuring isothermal reaction conditions with the conventional technology requires a considerable expenditure on equipment.

Calorimeters that permit isothermal experiment conditions may be divided into the following types: heat flow, heat balance and power compensation. The basis for these three calorimetric measuring methods is the heat flow balance of the reaction vessel. The required reaction heat as a function of time can be calculated via the heat flow balance, provided that all other components in the balance, especially the stirring energy, the heat flows through the reactor wall, and other heat loss flows, are known. All three types have in common the problem of the fluctuating heat transmission on the interior reactor wall during the course of a chemical reaction. Corresponding processes must be taken into account in the heat flow balance, either mathematically or experimentally. Experimental methods are always preferred over mathematical ones since the exact interrelationships are not known for a general system.

2. Description of Related Art

A calorimeter with an intermediate thermostat into which the reactor is built in, as well as with an external thermostat, has become known in the prior art from German patent application DE-A-3049105. It essentially consists of a reactor with an agitator wherein isothermal conditions are maintained during the course of a reaction by means of a regulated heater. An apparatus is used to measure the electrical output that is required to maintain the isothermal conditions. This calorimeter operates according to the above-mentioned principle of the so-called power compensation. The temperature is highest inside the reactor and a median temperature exists in the intermediate thermostat. The lowest temperature is inside the main thermostat. In accordance with the constant temperature difference between the reactor and the intermediate thermostat, a heat flux flows from the reactor into the intermediate thermostat, and a further heat flux flows from the intermediate thermostat into the main thermostat. When a reaction starts in the reactor, a regulator that is connected to a heater ensures that the temperature difference between the reactor and intermediate thermostat remains constant during the course of the reaction, despite the beginning reaction heat. An intermediate thermostat wall is formed by a tube coil system, through which the thermostat liquid of the main thermostat flows in a turbulent flow. The thermostat liquid usually is a liquid heat carrier that flows around the reaction vessel on the outside and can be regulated to a desired temperature. Permitting the thermostat liquid to flow around the reactor requires a double jacket. A double jacket of this type poses the problem, in particular, that local inhomogenities may occur within the same. Furthermore, the production and thermoregulation of a double-walled reaction vessel are expensive. Performing applications under pressure is difficult or impossible. A further shortcoming lies in the fact that the reactor volume is comparatively large, and correspondingly large quantities of the test substance must be produced. The large dimensions and complexity of the thermoregulating system have as a result that parallel operations would be expensive.

A further calorimeter is revealed in U.S. Pat. No. 4,456,389. This calorimeter is also provided with a double jacket containing a thermostat liquid that is circulated by means of a pump. This calorimeter permits isothermal experiment conditions, however, it has a comparatively large volume. The heat flow principle that is used here results in comparatively sluggish equipment with respect to quickly changing heat flows. The above-mentioned problem of the fluctuating heat transmission of the interior reactor wall during the reaction cannot be fully experimentally addressed with this calorimeter. Parallel operations would be expensive for reasons analogous to the above example.

The invention has as its object to create a calorimeter of the above type that avoids the above-mentioned problems. The inventive calorimeter shall be implementable with a significantly more simple design and nevertheless provide exact measurements. Furthermore, it shall be possible to equip it, in a simple manner, with further analysis methods such as, for example, an IR sensor.

BRIEF SUMMARY OF INVENTION

The invention is solved according to claim 1. In the inventive calorimeter the intermediate thermostat is essentially formed by a metal block. The double-walled reaction vessel that has been customary for a long time and the equipment required for circulating the cooling medium are not necessary with the inventive calorimeter. The thermostat liquid that used to be customary until now is replaced in the inventive reactor by the metal block. The reaction vessel can essentially be implemented by means of a simple bore in the metal block. A significant advantage of the inventive calorimeter is also seen in the fact that, e.g., an IR ATR sensor can be inserted laterally in a simple manner through a simple bore in the metal block, and that the sensor that is immersed into the reaction vessel is simultaneously brought to the right temperature by the metal block. The heat flow through the sensor, therefore, no longer needs to be treated separately from the heat flow through the reactor wall. The inventive calorimeter furthermore permits applications under pressure and applications with very small quantities of a test substance. The overall size of the calorimeter may be kept very small, thus also rendering parallel experiments possible without problems.

Further advantageous features will become apparent from the dependent claims, from the description below, as well as from the drawing.

DETAILED DESCRIPTION OF THE INVENTION

An embodiment of the invention, which is preferably designed for isothermal experiment conditions, will be explained below based on the single FIGURE. The FIGURE shows a schematic section through an inventive calorimeter. The calorimeter has a reactor 1 with an interior reactor space 15 that is built into an intermediate thermostat 2. The intermediate thermostat 2 is built onto an external thermostat 3 and has a metal block 4 which, with a reactor bore 16, forms the interior reactor space 15. An IR sensor 11 may be inserted through a lateral bore 19 into the interior reactor space 15 and sealed off pressure-tight. The metal block 4 is insulated on the outside with insulation material 17. The reactor bore 16 may be provided, on its inside, with a reactor jacket 12, which is preferably composed of an inert material, for example tetrafluoroethylene or enamel. Embodiments in which the reactor wall 12 is formed directly by the metal block 4 are conceivable as well. A metal block of this type may be made of steel, for example, or some other metal alloy or metal. A suitable material for the metal block is aluminum, for example, which generally requires a reactor jacket 12. The material for the metal block 4 should be specifically sturdy and heat conducting. Also suitable may be silver, as well as copper and corresponding alloys. The reactor jacket 12 is specifically a plastic coating of a plastic that is as inert as possible. An enamel coating is conceivable as well.

During a potential experiment, a test substance 20 is located in the interior space 15, for example a solution that is stirred with an agitator 6, which essentially incorporates a drive 13, a stirrer 14, as well as a coupling 9 between the drive 13 and the stirrer 14. The coupling 9 is preferably a magnetic coupling or a floating ring seal. Flow breakers 30 are provided for an optimal thorough mixing. The interior space 15 is closed with a cover 34 on which a guide member 35 is located for the stirrer 14. Through a channel 18 that leads to the outside, the starting substances, for example, can be introduced. Additional channels may be used, for example, for pressure measurements or the addition of inert gas. Into the test substance 20 or into the interior space 15 of the reactor, respectively, extends a controlled electric compensation heater 7, as well as a temperature sensor 8. The heater 7 and temperature sensor 8, together with a temperature regulator 21 and a power output meter 22, form a first control loop A. By means of this control loop A, which may also be referred to as an interior thermostat, the interior reactor temperature is regulated to a constant value. This regulation can take place very quickly since, first of all, the inertness of the testing substance 20 can be kept comparatively low based on its small volume, and, secondly, the heater 7, which may have a heating wire 7a, for instance, can respond very quickly to changes in the temperature. The electrical energy of the heater that is required to regulate the temperature is recorded during the entire measurement as a heat signal. The regulating frequency may be 10 Hz, for example. The temperature in the interior space of the reactor, or in the test substance 20, respectively, is thus kept constant through the control loop A. The output of the heater 7 that is required for this is included in the heat balance of the calorimeter as a heat flow. As can be seen, the temperature regulator 21 is connected via a signal line 23 to the power output meter 22. The power supply for the heater 7 is provided via a line 24.

The intermediate thermostat 2 has Peltier elements 5 that are connected in a thermally conducting manner to the metal block 4, as well as to a heat exchanger 31. The intermediate thermostat 2 preferably forms a heating as well as a cooling element. This is made possible by the Peltier elements 5 in a manner known per se. The metal block 4 can thus both be cooled as well as heated via the intermediate thermostat 2.

The external thermostat 3 incorporates a heat exchanger 31 that is connected in a thermally conducting manner to the Peltier elements 5. A tube 32 connects the heat exchanger 31 to a cryostat 33, for example, or to cooling water.

The temperature of the heat exchanger 31 does not need to be regulated. This is not necessary because the Peltier elements 5 can adjust variable temperature differences both up and down starting from the temperature of the heat exchanger. The only requirement for the heat exchanger 31 is that it must have a sufficiently large cooling capacity and that the temperature fluctuations during an experiment must not be greater than approximately 2° C. The temperature of the heat exchanger 31 may be measured with an additional temperature sensor 10. The temperature of the metal block 4 is regulated isothermally by means of a second control loop B. This control loop B has a temperature sensor 25 that measures the temperature of the metal block 4 and routes it via a line 26 to a temperature regulator 27. A plurality of temperature sensors may also be used in lieu of a temperature sensor 25. They may be used to measure a temperature distribution in the metal block, which, in principle, permits the performance of non-isothermal experiments. The regulator 27 is connected via a line 28 to a power output meter 29, as well as to the Peltier elements 5. The metal block 4, with respect to its isothermal regulation, has a somewhat greater inertness than a customary thermostat liquid. However, since the regulator needs to compensate merely for changes in the heat transmission on the interior reactor wall, the required speeds are sufficient. A time delay could be offset mathematically, if required.

The following conditions apply for the temperatures of the test substance 20, the metal block 4, as well as the heat exchanger 31, during an isothermal experiment:

1. Temperature test substance−temperature metal block= $\Delta TR$
2. $\Delta TR > 0$.
3. Both the temperature of the test substance 20, as well as the temperature of the metal block 4 are kept constant by the two control loops A and B.
    The following thus applies:
    $\Delta TR$=constant.
4. The temperature of the heat exchanger 31 fluctuates by maximally +/−2° C.
5. The temperature of the heat exchanger 31 is largely irrelevant within a certain range. It may, for example, differ from the temperature of the metal block 4 by −100° to +200° C.

With the calorimeter, a second thermal signal is thus measured in addition to the output signal of the compensation heater 7. It corresponds to the output that is required by the Peltier elements 5 to isothermally regulate the temperature of the metal block 4. The two measured electrical outputs may be described as follows:

1. The output of the compensation heater 7 that is required to keep the temperature of the test substance 20 constant, contains the sum of the reaction output and heat flow through the interior reactor wall.
2. The output of the Peltier elements 5 that is required to keep the temperature of the metal block 4 constant, contains the heat flow through the interior reactor wall. It is independent from the reaction output.

The desired experimental separation of the above two heat flows is thus possible. It is thus also possible to measure changes in the heat transmission on the reactor wall and take them into account in the heat flow balance. The above measuring principle based on the compensation heater 7 and the heat flow measurement by means of Peltier elements 5 can be implemented in a very simple manner and within a small space. Due to the direct heating or cooling of the metal block and interior of the reactor by means of electrical heating or cooling elements, respectively, regulating the corresponding temperatures also becomes very simple. The order of magnitude of the total volume of the equipment is 0.5 m×0.2 m×0.2 m, for example. A plurality of calorimeters of this type can easily be housed in one fume cupboard. Furthermore, the heat exchanger 31 can be designed in such a way that a plurality of calorimeters are operated at the same time and parallel operations become possible. With parallel operations of this type, a plurality of reactors are connected in series in a simple manner on a common, appropriately sized external thermostat. In this case it is essential that the metal blocks of the reactors can be regulated to different temperatures. This is essential especially as the reactors each have their own intermediate thermostat.

What is claimed is:

1. A calorimeter comprising:

a reactor;

an interior thermostat including a compensation heater and a first temperature sensor in said reactor, said interior thermostat further including a temperature regulator connected to said first temperature sensor for receiving a temperature indication from said first temperature sensor, an output meter connected to said compensation heater for supplying power thereto and a signal line connecting said temperature regulator to said output meter for supplying a control signal from said temperature regulator to said output meter;

an intermediate thermostat having, as a heat carrier, a metal block into which said reactor is built, a second temperature sensor embedded in said metal block for measuring the temperature of said metal block and a temperature regulator connected to receive a temperature indication from said second temperature sensor, said intermediate thermostat further having a power output device connected to said temperature regulator, and a heating and/or cooling element connected to said temperature regulator, the temperature of said metal block being regulated by the heating and/or cooling element and the energy required from said heating and/or cooling element for the regulation being recorded and entering into the heat flow balance of the calorimeter as heat flow; and an external thermostat with which said intermediate thermostat cooperates, wherein, in said interior thermostat, the temperature of a test substance in said reactor is measured by said first temperature sensor and regulated by said compensation heater, wherein a heat input from said compensation heater enters into the heat flow balance of the calorimeter as heat flow.

2. The calorimeter according to claim 1, wherein the heating and/or cooling elements are Peltier elements.

3. The calorimeter according to claim 1, further comprising an agitator disposd in said reactor and connected to a drive member by a magnetic coupling or a floating ring seal.

4. The calorimeter according to claim 1, further comprising a sensor for chemical and/or physical measurements inserted into said metal block to be brought to a predetermined temperature by said metal block.

5. The calorimeter according to claim 1, comprising a plurality of reactors built onto a common external thermostat.

6. The calorimeter according to claim 1, wherein said metal block has a portion that is located below said reactor and said second temperature sensor is embedded in said portion.

* * * * *